United States Patent
Mondal

(10) Patent No.: US 9,388,092 B2
(45) Date of Patent: Jul. 12, 2016

(54) PERFORMANCE OF GA- AND ZN-EXCHANGED ZSM-5 ZEOLITE CATALYST FOR CONVERSION OF OXYGENATES TO AROMATICS

(71) Applicant: Saudi Basic Industries Corporation, Riyadh (SA)

(72) Inventor: Kartick Chandra Mondal, Vadodara (IN)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 0 days.

(21) Appl. No.: 13/717,010

(22) Filed: Dec. 17, 2012

(65) Prior Publication Data
US 2013/0158323 A1 Jun. 20, 2013

(30) Foreign Application Priority Data
Dec. 20, 2011 (EP) .................................. 11009991

(51) Int. Cl.
*C07C 1/20* (2006.01)
*B01J 29/40* (2006.01)
*B01J 37/02* (2006.01)
*B01J 29/87* (2006.01)

(52) U.S. Cl.
CPC . *C07C 1/20* (2013.01); *B01J 29/40* (2013.01); *B01J 29/87* (2013.01); *B01J 37/02* (2013.01); *C07C 2523/06* (2013.01); *C07C 2523/08* (2013.01); *C07C 2523/10* (2013.01); *C07C 2523/26* (2013.01); *C07C 2523/28* (2013.01); *C07C 2523/30* (2013.01); *C07C 2529/40* (2013.01)

(58) Field of Classification Search
CPC .............. C07C 1/20; C07C 1/24; C07C 1/00; C07C 1/02; C07C 1/04
USPC ................................................. 585/638–642
See application file for complete search history.

(56) References Cited

U.S. PATENT DOCUMENTS 4,490,569 A   12/1984  Chu et al.
4,686,312 A * 8/1987  Chu et al. ...................... 585/315
6,372,680 B1   4/2002  Wu et al.
8,450,548 B2   5/2013  Karim et al.
2008/0216391 A1* 9/2008  Cortright ................. C10G 3/45
                                                44/307

FOREIGN PATENT DOCUMENTS

CN    101671226 A    3/2010
WO    2004087624 A1  10/2004
WO    2009021726 A1  2/2009

OTHER PUBLICATIONS

Extended European Search Report; European Application No. 11009991.8; Date of Mailing: May 14, 2012; 7 Pages.
Chinese Patent No. 101671226; Date of Publication: Mar. 17, 2010; Abstract Only; 1 page.
International Search Report for International Application No. PCT/EP2012/005213; Date of Mailing: May 14, 2013; 3 pages.
Written Opinion of the International Searching Authority for International Application No. PCT/EP2012/005213; Date of Mailing: Jun. 24, 2014; 4 pages.
Wolfgang Holderich et al., "Zeolites: Catalysts for Organic Syntheses" Angew. Chem. Int. Ed. Engl. 27 (1988) pp. 226-246; 21 pages.
Molecular Sieves; Kirk-Othmer Encyclopedia of Chemical Technology; Fifth Edition, vol. 16; 24 Pages.
Yoshio Ono et al.; "Selective Conversion of Methanol into Aromatic Hydrocarbons over Zinc-exchanged ZSM-5 Zeolites"; J. Chem. Soc., Faraday Trans. 1; vol. 84, Issue 4; 1988; pp. 1091-1099; 9 pages.
Hans Schulz; "Coking of Zeolites During Methanol Conversion: Basic Reactions of the MTO-, MTP- and MTG Processes"; Catalysis Today; vol. 154; 2010; pp. 183-194; 12 pages.
Paul B. Weisz, "Polyfunctional Heterogeneous Catalysis" Socony Mobil Oil Company, Incorporated; Research Department, Paulsboro, New Jersey, pp. 137-190; 54 pages.

* cited by examiner

Primary Examiner — In Suk Bullock
Assistant Examiner — Sharon Pregler
(74) Attorney, Agent, or Firm — Cantor Colburn LLP

(57) ABSTRACT

The present invention relates to a process for producing aromatic hydrocarbons comprising contacting a feedstream comprising an oxygenate with a catalyst composition comprising a medium pore-size aluminosilicate zeolite further comprising gallium and one or more elements selected from Group 12 of the Periodic Table. The process of the present invention is preferably performed in absence of any feed diluents.

18 Claims, No Drawings

PERFORMANCE OF GA- AND ZN-EXCHANGED ZSM-5 ZEOLITE CATALYST FOR CONVERSION OF OXYGENATES TO AROMATICS

CROSS REFERENCE TO RELATED APPLICATION

This application claims priority to European Patent Application Serial No. 11009991.8, filed Dec. 20, 2011, which is herein incorporated by reference in its entirety.

The present invention relates to a process for producing aromatic hydrocarbons, particularly aromatic hydrocarbons having 6-8 carbon atoms, by the catalytic conversion of an oxygenate using a medium pore-size aluminosilicate zeolite catalyst having acidic and dehydrogenation functionality.

It has been previously described that oxygenates can be directly converted into a product stream comprising aromatic hydrocarbons using zeolite-based catalyst.

U.S. Pat. No. 6,372,680 B1 (2002) describes a catalyst system comprising a first solid material comprising SAPO-34 and a second solid material comprising ZSM-5 zeolite and a compound containing Zn and a metal selected from Group IIIA and Group VIB for the conversion of oxygenated hydrocarbon to aromatics.

Ono (1988) J Chem Soc Faraday Trans 1 84(4) 1091-1099 describes the use of Zn-exchanged H-ZSM-5 and Ga-exchanged H-ZSM-5 for the selective conversion of methanol to aromatics. The yield of aromatic hydrocarbons is improved by depositing Ga or Zn on the H-ZSM-5. Ono does not describe catalysts comprising both Zn and Ga.

A drawback of conventional zeolite-based catalyst useful in the aromatization of oxygenates is that the selectivity for aromatics is relatively low. Furthermore, it was found that catalyst activity of conventional zeolite-based catalyst in alkane aromatization process is reduced over time.

It was an object of the present invention to provide a process for the aromatization of oxygenates, having an improved selectivity for useful aromatic hydrocarbons, such as BTX, and wherein the catalyst activity is more stable.

The solution to the above problem is achieved by providing the embodiments as described herein below and as characterized in the claims. Accordingly, the present invention provides a process for converting oxygenates into aromatic hydrocarbons, particularly aromatic hydrocarbons having 6-8 carbon atoms, comprising contacting a feedstream comprising at least one oxygenate compound with a catalyst comprising a medium pore-size aluminosilicate zeolite further comprising gallium (Ga) and one or more elements selected from Group 12 of the Periodic Table.

In the context of the present invention, it was found that the selectivity for aromatics and for BTX in particular can be increased to 70.4 wt-% and 60 wt-%, respectively, when using the process of the present invention wherein the medium pore-size zeolite comprised in the catalyst composition comprises about 0.02-2 wt-% Ga and 0.02-2 wt-% Zn with respect to the total zeolite. Moreover, the present invention achieved C6 to C8 aromatics yield of 88.2% (considering on total aromatic 'C' % only) at 430° C. and WHSV 4 h$^{-1}$ (contact time W/F=8 ghmol$^{-1}$) which is superior to the catalyst performance in oxygenate aromatization processes reported in the prior art.

Without being bound to theory, it is believed that this synergistic effect of the presence of both Ga and the Group 12 element in catalyst composition has an advantageous influence on the hydrogen transfer reaction for the formation of alkenes, which subsequently aromatize in the zeolitic cage to form the C6 to C8 aromatic hydrocarbons. Moreover, it is believed that the Group 12 species comprised in the catalyst composition increases dehydrogenation activity which leads to the formation of more aromatic hydrocarbons rather aliphatic hydrocarbons and other $CO_x$ process products.

The herein-described synergistic effect of Ga and the Group 12 element appears to be based on the close proximity of the Ga and the Group 12 element with the zeolitic protons at the zeolitic channel intersections. Accordingly, it is preferred that the process of the present invention comprises contacting the feedstream with a catalyst comprising a medium pore-size aluminosilicate zeolite catalyst, wherein Ga and one or more Group 12 elements are in close proximity with the zeolitic protons at the zeolitic channel intersections. Means and methods of preparing such a preferred catalyst are well-known in the art; see e.g. Weisz (1963) Advances in Catalysis 13, Academic Press, London, p. 137.

The present invention provides a process for converting oxygenates into aromatic hydrocarbons. The feedstream used in the present process preferably comprises less than 30 mol-% of non-oxygenate components (i.e. components which are not an oxygenate compound as defined herein below). More preferably, the feedstream comprises less than 20 mol-% of non-oxygenate components, particularly preferably less than 10 mol-% of non-oxygenate components, and most preferably less than 5 mol-% of non-oxygenate components.

It was further surprisingly found that the process of the present invention can be carried out in absence of any feed diluents. This will eliminate the downstream diluents separation step leading to the reduction of overall operation cost and increases the throughput for a given size of reactor. In a preferred embodiment of the present invention, accordingly, the process of the present invention is performed wherein More preferably, the feedstream comprises less than 30 mol-% of diluents (i.e. inert components which do not undergo chemical conversion in the reactor). More preferably, the feedstream comprises less than 20 mol-% of diluents, particularly preferably less than 10 mol-% of diluents, and most preferably less than 5 mol-% of diluents.

As used herein, the term "zeolite" or "aluminosilicate zeolite" relates to an aluminosilicate molecular sieve. An overview of their characteristics is for example provided by the chapter on Molecular Sieves in Kirk-Othmer Encyclopedia of Chemical Technology, Volume 16, p 811-853; in Atlas of Zeolite Framework Types, 5th edition, (Elsevier, 2001). The term "medium pore sized zeolite" as used herein is very well-known in the art; see e.g. Holderich et al. (1988) Angew. Chem. Int. Ed. Engl. 27:226-246. Accordingly, a medium pore size zeolite is a zeolite having a pore size of about 5-6 Å. Suitable medium pore size zeolites are 10-ring zeolites, i.e. the pore is formed by a ring consisting of 10 $SiO_4$ tetrahedra. Large pore size zeolites have a pore size of about 6-8 Å and are of the 12-ring structure type. Zeolites of the 8-ring structure type are called small pore size zeolites. In the above cited Altlas of Zeolite Framework Types various zeolites are listed based on ring structure. Most preferably the zeolite is ZSM-5 zeolite, which is a well-known zeolite having MFI structure. ZSM-5 zeolite has an ellipsoidal pore size of 5.5×5.6 Å.

Preferably, the silica ($SiO_2$) to alumina ($Al_2O_3$) molar ratio of the zeolite is in the range of about 10-200. In the context of the present invention it was found that the performance and stability of the catalyst in the process of the present invention can be improved when the zeolite comprised in said catalyst has a silica to alumina molar ratio of about 10-200. Zeolites having a silica to alumina molar ratio of 10-200 are well known in the art and also are commercially available. Means and methods for quantifying the silica to alumina molar ratio of a zeolite are well known in the art and include, but are not limited to AAS (Atomic Absorption Spectrometer) or ICP (Inductively Coupled Plasma Spectrometry) analysis.

Preferably, the catalyst used in the process of the present invention comprises 0.1-1.5 wt-% Ga with respect to the total zeolite and most preferably 0.5-1.2 wt-% Ga with respect to the total zeolite.

As used herein, the term "elements selected from Group 12 of the Periodic Table" or "Group 12 element" indicates the group of element comprised in Group 12 of the IUPAC Periodic Table. Preferably, the Group 12 element is selected from the group consisting of zinc (Zn), cadmium (Cd) and mercury (Hg) and more preferably from the group consisting of zinc (Zn) and cadmium (Cd). Most preferably, the Group 12 element is zinc (Zn). Preferably, the catalyst used in the process of the present invention comprises 0.1-1.5 wt-% Group 12 element with respect to the total zeolite and more preferably 0.5-1.2 wt-% Group 12 element with respect to the total zeolite.

Preferably, the catalyst used in the process of the present invention further comprises one or more promoter elements. Said promoter element is preferably one or more elements selected from the group consisting of one or more elements selected from the lanthanide elements or Group 6 of the Periodic Table. The term "lanthanide element" or "lanthanide" or "lanthanoid" as used herein is very well known in the art and describes the fifteen metallic chemical elements with atomic numbers 57 through 71, from lanthanum (La) through lutetium (Lu). Preferably, the lanthanide element that may be comprised in the catalyst used in the process of the present invention is lanthanum (La). As used herein, the term "elements selected from Group 6 of the Periodic Table" or "Group 6 element" indicates the group of element comprised in Group 6 of the IUPAC Periodic Table. Preferably, the Group 6 element is selected from the group consisting of chromium (Cr), Molybdenum (Mo) and tungsten (W). Most preferably, the Group 12 element is tungsten (W). The most preferred promoter element is La. In case a promoter element is present, it is preferred that the catalyst comprises 0.005-1 wt-% of each of the promoter element with respect to the total Ga—Zn-zeolite, more preferably between 0.01-0.1 wt-% and most preferably between 0.02-0.07 wt-% of each promoter element.

The introduction of the active elements on the zeolite can be carried out by ion exchange or by impregnation. In these catalyst preparation methods, the $NH_4$-form of the zeolite is converted to the modified form (e.g. to Ga—Zn-exchanged zeolite). Accordingly, it is preferred that the zeolite is in the $NH_4$-form before the elements are deposited on said zeolite: i.e. having at least a portion of the original cations associated therewith replaced by $NH_4^+$ ion. Methods to convert an aluminosilicate zeolite to the $NH_4$-form are well known in the art.

Preferably, the Ga and one or more Group 12 elements are introduced on the zeolite by ion exchange. Even more preferably, all active elements comprised in the zeolite are introduced by ion-exchange. Accordingly, it is preferred that the bifunctional zeolite catalyst used in the process of the present invention comprises a medium pore-size aluminosilicate zeolite that is modified to comprise Ga and one or more Group 12 elements by ion-exchange. As a result thereof, the Gallium (Ga) and Group 12 element, which are present in the zeolite channels are in a close vicinity of the zeolitic protonic acid sites. During the ion-exchange process with $NH_4$-ZSM-5 zeolite, Ga and Zn occupy in the non-framework sites; see e.g. Weisz (1963) Advances in Catalysis 13, Academic Press, London, p. 137. Without being bound by theory, it is believed that by preparing the bifunctional zeolite catalyst by an ion-exchange process there is an improved interaction between the zeolitic protonic acid sites and the Ga and the Group 12 element metal sites. Other methods suitable for preparing zeolite catalyst comprising Ga and one or more Group 12 elements, such as impregnation, are believed to lead to a weaker metal-support interaction. As a result thereof, large metal particles may be obtained, which is less preferred as the Ga and the Group 12 element then to a much lesser extent are in close proximity with the zeolitic protons at the zeolitic channel intersections.

In one embodiment, the present invention provides a process comprising preparing a catalyst comprising a medium pore-size aluminosilicate zeolite further comprising gallium (Ga) and one or more elements selected from Group 12 of the Periodic Table wherein the Ga and one or more Group 12 elements are introduced on the zeolite by ion-exchange as described herein and a step of contacting a feedstream comprising at least one oxygenate compound with a catalyst as described herein.

As used herein, the term "aromatic hydrocarbon" or "aromatic" refers to cyclically conjugated hydrocarbon with a stability (due to delocalization) that is significantly greater than that of a hypothetical localized structure (e.g. Kekulé structure). The most common method for determining aromaticity of a given hydrocarbon is the observation of diatropicity in the $^1H$ NMR spectrum. Preferably, the aromatic hydrocarbons produced in the process of the present invention are aromatic hydrocarbons having between 6 and 8 carbon atoms (C6-C8 aromatics). More preferably, the hydrocarbons produced in the process of the present invention are BTX, which is a commonly known abbreviation of a mixture of benzene, toluene and xylenes.

As used herein, the term "oxygenate" or "oxygenate compound(s)" relates to refers to chemical compounds containing oxygen as a part of chemical structure, usually in the form of alcohol or ether. Preferred oxygenates or oxygenate compound(s) used in the process of the present invention are selected from the group consisting of methanol, ethanol, n-butanol, dimethyl ether (DME), and diethyl ether (DEE).

The process of the present invention is performed under process conditions effective to produce product stream comprising aromatic hydrocarbons These process conditions useful in the process of the present invention, also described herein as "oxygenate aromatization conditions", can be easily determined by the person skilled in the art; see e.g. Petroleum Technology Vol. 2 (2007) Wiley-Interscience p. 338-345 and Schulz (2010) Catalysis Today 154: 183-194. Accordingly, the oxygenate aromatization conditions include a temperature of 350-500° C., a pressure of atmospheric-500 kPa gauge and a weight hourly space velocity of 1-10 $hr^{-1}$. Preferably, the aromatization conditions include a temperature of 430-480° C.

MODE(S) FOR CARRYING OUT THE INVENTION

The present invention will now be more fully described by the following non-limiting Examples.

EXAMPLE 1

Preparation of Ga-Exchanged ZSM-5 Zeolite 0.5952 g of gallium nitrate was dissolved in 200 ml demineralized water in a 3-neck round bottom flask. 10 g of dry ZSM-5 in $NH_4$ form, having a Si/Al ratio of 25 was added. The mixture was heated to 90-95° C. and stirred at 300 rpm for 24 hours.

The Ga-exchanged ZSM-5 was filtered out and washed with 2 l of demineralized water. Dried the whole mass at 120° C. overnight and then calcined the material at 600° C. for 4 h (using 2° C./min ramp). This procedure can be applied to prepare Ga-exchanged ZSM-5 with other Si/Al ratios.

EXAMPLE 2

Preparation of Ga—Zn-Exchanged ZSM-5 Zeolite

Required amount of gallium nitrate and zinc nitrate were dissolved in 200 ml demineralized water in a 3-neck round bottom flask. 10 g of dry ZSM-5 in $NH_4$ form, having a Si/Al ratio of 25 was added. The mixture was heated to 90-95° C. and stirred at 300 rpm for 24 hours.

The Ga—Zn-exchanged ZSM-5 was filtered out and washed with 2 l of demineralized water. Dried the whole mass at 120° C. overnight and then calcined the material at 600° C. for 4 h (using 2° C./min ramp).

This procedure can be applied to prepare different amount of Ga—Zn-exchanged ZSM-5 with other Si/Al ratios.

EXAMPLE 3

Preparation of La—Ga—Zn-Exchanged ZSM-5 Zeolite 0.5952 g of gallium nitrate, 0.4555 g of zinc nitrate and 0.00095 g of lanthanum nitrate were dissolved in 200 ml demineralized water in a 3-neck round bottom flask. 10 g of dry ZSM-5 in $NH_4$ form, having a Si/Al ratio of 25 was added. The mixture was heated to 90-95° C. and stirred at 300 rpm for 24 hours.

The La—Ga—Zn-exchanged ZSM-5 was filtered out and washed with 2 l of demineralized water. Dried the whole mass at 120° C. overnight and then calcined the material at 600° C. for 4 h (using 2° C./min ramp). The nominal Ga, Zn and La content of the zeolite were determined by AAS to be 1 wt-%, −1 wt-% and 0.05 wt-% respectively.

This procedure can be applied to prepare Ga—Zn-exchanged ZSM-5 with other promoters like W, Mo, lanthanide elements and other Si/Al ratios.

EXAMPLE 4

Catalytic Process of the Present Invention

This example illustrates the catalytic process of the present invention for the low temperature conversion of methanol to aromatic hydrocarbon in particular C6-C8 aromatic hydrocarbon in the absence of any feed diluent over Ga- and/or Zn-exchanged ZSM-5 zeolite catalysts. A conventional tubular SS316 reactor with ¾ inch OD and 0.083 mm wall thickness packed with the zeolite catalyst of 0.25-0.5 mm (35-60 mesh size) particles and kept in the tubular electrical furnace such that the catalyst is in a constant temperature zone of the furnace, was used for illustrating the process. The catalytic process is carried out by passing continuously methanol over the zeolite catalyst in absence of any feed diluent at the process conditions. The reactor or reaction temperature was measured by Chromel-Alumel thermocouple located axially in the catalyst bed. The reaction gaseous products after the removal of water and liquid hydrocarbons formed in the reaction by condensation at −8° C., the liquid hydrocarbons was analyzed offline after separating the water and gaseous products including $CO_x$ were analyzed online using thermal conductivity and flame ionized detectors.

This example further illustrate the process of this invention, using, Ga- and/or Zn-exchanged ZSM5 zeolite catalyst (with Si/Al=25) with different Ga- and/or Zn-loading given in Table 1 & Table 2.

TABLE 1

Methanol-to-aromatics conversion over Ga- and/or Zn-exchanged ZSM-5 catalyst at reaction temperature 450° C. and WHSV = 9 $h^{-1}$

| | | Hydrocarbon product distribution - Selectivity wt-% [Considering total C %] | | | | | |
|---|---|---|---|---|---|---|---|
| Catalyst | Time (min) | C1-C2 | C3 | C4+ | $C_6$-$C_8$ Aromatics | C9+ aromatics | CO + $CO_2$ |
| 1 wt-% Ga/$NH_4$ZSM-5 | 120 | 15.8 | 24.8 | 17.7 | 31.7 | 2.5 | — |
| 1 wt-% Ga + 1 wt-% Zn/$NH_4$ZSM-5 | 120 | 9.4 | 19.4 | 15.4 | 41.7 | 5.5 | 1.3 |
| 2 wt-% Ga + 1 wt-% Zn/$NH_4$ZSM-5 | 120 | 27.6 | 22.6 | 15.7 | 21.9 | 4.5 | 3.8 |
| 1 wt-% Ga + 2 wt-% Zn/$NH_4$ZSM-5 | 120 | 35.3 | 22.0 | 11.1 | 12.5 | 2.8 | 14.1 |
| 2 wt-% Ga + 2 wt-% Zn/$NH_4$ZSM-5 | 120 | 32.6 | 21.3 | 12.5 | 15.5 | 3.4 | 12.1 |
| 1 wt-% Ga + 0.5 wt-% Zn/$NH_4$ZSM-5 | 120 | 15.7 | 18.1 | 11.2 | 40.4 | 6.1 | 3.0 |

TABLE 2

Methanol-to-aromatics conversion over 1 wt-% Ga and 1 wt-% Zn exchanged ZSM-5 catalyst at different reaction temperatures and WHSV = 9 $h^{-1}$

| | | | Hydrocarbon product distribution - Selectivity wt-% [Considering total C %] | | | | | |
|---|---|---|---|---|---|---|---|---|
| Catalyst | Time (min) | Temp (° C.) | C1-C2 | C3 | C4+ | $C_6$-$C_8$ Aromatics | C9+ aromatics | CO + $CO_2$ |
| 1 wt-% Ga + 1 wt-% Zn/$NH_4$ZSM-5 | 120 | 430 | 14.1 | 28.5 | 3.1 | 36.8 | 5.7 | 3.8 |
| 1 wt-% Ga + 1 wt-% Zn/$NH_4$ZSM-5 | 120 | 450 | 9.4 | 19.4 | 15.4 | 41.7 | 5.5 | 1.3 |
| 1 wt-% Ga + 1 wt-% Zn/$NH_4$ZSM-5 | 120 | 477 | 21.6 | 18.4 | 11.0 | 34.1 | 5.6 | 5.1 |

EXAMPLE 5

Effect of WHSV

This example further illustrate the process of this invention using Ga—Zn-exchanged ZSM-5 (Si/Al=25, Ga-loading: 1 wt-%, Zn-loading: 1 wt-%) zeolite catalyst. Catalyst was synthesized and composition particles of 0.25-0.5 mm as prepared and loaded to the reactor as under Example 2 and Example 4, respectively.

The experimental set up, reaction and analysis procedure of Example 4 is repeated, with the exception that the WHSV of methanol are different. Each set of reaction was carried out over fresh catalyst.

The results are shown in Table 3.

TABLE 3

Methanol-to-aromatics conversion over 1 wt-% Ga and 1 wt-% Zn exchanged ZSM-5 catalyst at different methanol space velocity and reaction temperature = 450° C.

| | | | Hydrocarbon product distribution - Selectivity wt-% [Considering total C %] | | | | | |
|---|---|---|---|---|---|---|---|---|
| Catalyst | Time (min) | WHSV ($h^{-1}$) | C1-C2 | C3 | C4+ | $C_6$-$C_8$ Aromatics | C9+ aromatics | CO + $CO_2$ |
| 1 wt-% Ga + 1 wt-% Zn/ $NH_4$ZSM-5 | 120 | 9 | 9.4 | 19.4 | 15.4 | 41.7 | 5.5 | 1.3 |
| 1 wt-% Ga + 1 wt-% Zn/ $NH_4$ZSM-5 | 120 | 5 | 10.3 | 13.9 | 8.3 | 55.1 | 7.6 | 1.9 |
| 1 wt-% Ga + 1 wt-% Zn/ $NH_4$ZSM-5 | 120 | 4 | 8.3 | 11.8 | 7.6 | 56.3 | 8.1 | 1.7 |
| 1 wt-% Ga + 1 wt-% Zn/ $NH_4$ZSM-5 | 120 | 3 | 6.3 | 12.2 | 8.2 | 60.4 | 8.4 | 1.9 |

EXAMPLE 6

Effect of Temperature

This example further illustrate the process of this invention using Ga and Zn exchanged ZSM-5 (Si/Al=25, Ga-loading: 1 wt-%, Zn-loading: 1 wt-%) zeolite catalyst. Catalyst was synthesized and composition particles of 0.25-0.5 mm as prepared and loaded to the reactor as under Example 2 and Example 4, respectively.

The experimental set up, reaction and analysis procedure of Example 4 is repeated, with the exception that the reaction temperatures are different with fixed WHSV=4 $h^{-1}$. Each set of reaction was carried out over fresh catalyst.

The results are shown in Table 4.

TABLE 4

Methanol-to-aromatics conversion over 1 wt-% Ga and 1 wt-% Zn exchanged ZSM-5 catalyst at different reaction temperatures and at a fixed WHSV = 4 $h^{-1}$

| | | | Hydrocarbon product distribution - Selectivity wt-% [Considering total C %] | | | | | |
|---|---|---|---|---|---|---|---|---|
| Catalyst | Time (min) | Temp (° C.) | C1-C2 | C3 | C4+ | $C_6$-$C_8$ Aromatics | C9+ aromatics | CO + $CO_2$ |
| 1 wt-% Ga + 1 wt-% Zn/ $NH_4$ZSM-5 | 120 | 450 | 8.3 | 11.8 | 7.6 | 56.3 | 8.1 | 1.7 |
| 1 wt-% Ga + 1 wt-% Zn/ $NH_4$ZSM-5 | 120 | 430 | 5.3 | 10.9 | 8.1 | 62.1 | 8.3 | 1.0 |

EXAMPLES 7

Effect of Promoters

This example further illustrate the process of this invention using La—Ga—Zn exchanged ZSM-5 (Si/Al=25, Ga-loading: 1 wt-%, Zn-loading: La-loading: 0.05-0.1 wt-%) and W—Ga—Zn exchanged ZSM-5 (Si/Al=25, Ga-loading: 1 wt-%, Zn-loading: W-loading: 0.03-0.1 wt-%) zeolite catalyst. Catalyst was synthesized and composition particles of 0.25-0.5 mm as prepared and loaded to the reactor as under Example 3 and Example 4, respectively.

The experimental set up, reaction and analysis procedure of Example 4 is repeated, with the exception that the reaction temperatures are different with fixed WHSV=4 $h^{-1}$. Each set of reaction was carried out over fresh catalyst.

The results are shown in Table 5.

TABLE 5

Methanol-to-aromatics conversion over 1 wt-% Ga and 1 wt-% Zn exchanged ZSM-5 catalyst promoted by 'La' or 'W' at WHSV = 4 $h^{-1}$

| Catalyst | Time (min) | Temp (° C.) | Hydrocarbon product distribution - Selectivity wt-% [Considering total C %] | | | | | |
|---|---|---|---|---|---|---|---|---|
| | | | C1-C2 | C3 | C4+ | $C_6$-$C_8$ Aromatics | C9+ aromatics | CO + $CO_2$ |
| 0.03 wt-% W + 1 wt-% Ga + 1 wt-% Zn/NH$_4$ZSM-5 | 120 | 430 | 5.6 | 11.4 | 9.9 | 59.7 | 7.8 | 0.7 |
| 0.03 wt-% W + 1 wt-% Ga + 1 wt-% Zn/NH$_4$ZSM-5 | 120 | 450 | 7.6 | 10.4 | 7.5 | 59.5 | 8.3 | 2.4 |
| 0.10 wt-% W + 1 wt-% Ga + 1 wt-% Zn/NH$_4$ZSM-5 | 120 | 450 | 7.6 | 11.4 | 10.1 | 55.4 | 8.0 | 2.9 |
| 0.05 wt-% La + 1 wt-% Ga + 1 wt-% Zn/NH$_4$ZSM-5 | 120 | 450 | 7.3 | 10.6 | 6.6 | 60.0 | 7.8 | 4.3 |
| 0.10 wt-% La + 1 wt-% Ga + 1 wt-% Zn/NH$_4$ZSM-5 | 120 | 450 | 9.0 | 11.6 | 7.7 | 56.7 | 9.0 | 3.0 |
| 0.05 wt-% La + 1 wt-% Ga + 1 wt-% Zn/NH$_4$ZSM-5 | 120 | 430 | 4.8 | 10.1 | 8.0 | 63.5 | 8.3 | 0.7 |

Comparative analysis of aromatics products over Ga and Zn exchanged ZSM-zeolite catalyst in presence and in absence of promoter at different reaction temperature and at a fixed WHSV=4 $h^{-1}$ given in Table 6.

TABLE 6

Comparative analysis

| Catalyst | Temp (° C.) | WHSV ($h^{-1}$) | Aromatics Selectivity wt-% [Considering aromatics C %] | |
|---|---|---|---|---|
| | | | Total C6-C8 | C9+ |
| 1 wt-% Ga + 1 wt-% Zn/NH$_4$ZSM-5 | 450 | 4 | 83.9 | 12.1 |
| 1 wt-% Ga + 1 wt-% Zn/NH$_4$ZSM-5 | 430 | 4 | 88.2 | 11.8 |
| 0.1 wt-% La/1 wt-% Ga + 1 wt-% Zn/NH$_4$ZSM | 430 | 4 | 88.9 | 11.6 |

The invention claimed is:

1. A process for converting oxygenates into aromatic hydrocarbons comprising
   contacting a feedstream comprising an oxygenate compound with a catalyst comprising a medium pore-size aluminosilicate zeolite further comprising gallium (Ga) and zinc (Zn); and
   converting the oxygenate compound to the aromatic hydrocarbon,
   wherein the oxygenate is selected from the group consisting of methanol, ethanol, n-butanol, dimethyl ether (DME), and diethyl ether (DEE),
   wherein the feedstream comprises less than 30 mol % of a non-oxygenate component.

2. The process of claim 1, wherein the medium pore-size zeolite is a zeolite having a pore size of 5.0-6.0 Å.

3. The process of claim 1, wherein the medium pore-size zeolite is ZSM-5.

4. The process of claim 1, wherein the zeolite has a silica (SiO$_2$) to alumina (Al$_2$O$_3$) molar ratio of 10-200.

5. The process of claim 1, wherein the catalyst comprises 0.1-1.5 wt-% Ga with respect to the total weight of the zeolite.

6. The process of claim 1, wherein the catalyst comprises 0.1-1.5 wt-% zinc with respect to the total weight of the zeolite.

7. The process of claim 1, wherein the catalyst further comprises a promoter element selected from the group consisting the lanthanide Series and Group 6 of the Periodic Table.

8. The process of claim 7, wherein the promoter element is selected from the group consisting of lanthanum (La), chromium (Cr), molybdenum (Mo) and tungsten (W).

9. The process of claim 7, wherein the catalyst comprises 0.005-1 wt-% of the promoter element with respect to the total weight of the Ga—Zn-zeolite.

10. The process of claim 1, wherein the Ga and zinc are introduced on the zeolite by ion-exchange.

11. The process of claim 1, wherein the process is performed under process conditions comprising a temperature of 350-500° C., a pressure of atmospheric-500 kPa gauge and a weight hourly space velocity of 1-10 $hr^{-1}$.

12. The process of claim 1, wherein the feedstream does not comprise any diluents.

13. The process of claim 1, wherein the product stream comprises aromatic hydrocarbons comprising 6-8 carbon atoms.

14. A process for converting oxygenates into aromatic hydrocarbons comprising contacting a feedstream comprising an oxygenate compound with a catalyst comprising a medium pore-size aluminosilicate zeolite further comprising gallium (Ga), zinc, and 0.005-1 wt % of a promote element based upon a total weight of the zeolite, wherein the promoter element is selected from the group consisting of lanthanum (La), chromium (Cr), molybdenum (Mo) and tungsten (W); and converting the oxygenate compound to the aromatic hydrocarbon;

wherein the feedstream comprises less than 30 mol % of a non-oxygenate component.

15. The process of claim 1, wherein the feedstream comprises less than 20 mol % of the non-oxygenate component.

16. The process of claim 15, wherein the feedstream comprises less than 15 mol % of the non-oxygenate component.

17. The process of claim 16, wherein the feedstream comprises less than 10 mol % of the non-oxygenate component.

18. The process of claim 14, wherein the feedstream comprises less than 20 mol % of the non-oxygenate component.

* * * * *